United States Patent
Chen et al.

(10) Patent No.: US 9,632,037 B2
(45) Date of Patent: Apr. 25, 2017

(54) THREE DIMENSIONAL PRINTING APPARATUS AND METHOD FOR DETECTING PRINTING ANOMALY

(71) Applicants: XYZprinting, Inc., New Taipei (TW); Kinpo Electronics, Inc., New Taipei (TW); Cal-Comp Electronics & Communications Company Limited, New Taipei (TW)

(72) Inventors: Peng-Yang Chen, New Taipei (TW); Wen-Ten Lin, New Taipei (TW)

( * ) Notice: Subject to any disclaimer, the term of this patent is extended or adjusted under 35 U.S.C. 154(b) by 390 days.

(21) Appl. No.: 14/287,207

(22) Filed: May 27, 2014

(65) Prior Publication Data

US 2015/0301517 A1    Oct. 22, 2015

(30) Foreign Application Priority Data

Apr. 18, 2014 (TW) .............................. 103114233 A (51) Int. Cl.
   *G01N 21/88*    (2006.01)
   *B33Y 50/02*    (2015.01)
   (Continued)

(52) U.S. Cl.
   CPC .......... *G01N 21/8851* (2013.01); *B33Y 10/00* (2014.12); *B33Y 30/00* (2014.12);
   (Continued)

(58) Field of Classification Search
   CPC ......... B33Y 10/00; B33Y 30/00; B33Y 50/02; G06T 1/00; G06T 5/006; G06T 5/50;
   (Continued)

(56) References Cited

U.S. PATENT DOCUMENTS 6,460,958 B2 * 10/2002 Kubo .................... B41J 3/4073
                                                        347/2
7,543,903 B2 *  6/2009 Little .................... B41J 25/005
                                                        347/19
(Continued)

FOREIGN PATENT DOCUMENTS

CN          203344505          12/2013
CN          104739513 A    *   7/2015
(Continued)

OTHER PUBLICATIONS

"Office Action of Taiwan Counterpart Application," issued on Jun. 23, 2015, p. 1-p. 5.
(Continued)

*Primary Examiner* — Crystal J Barnes-Bullock
(74) *Attorney, Agent, or Firm* — Jianq Chyun IP Office (57) ABSTRACT

A three dimensional printing apparatus and method for detecting printing anomaly are provided. The method is adapted to the three dimensional printing apparatus including an image sensor module and a movable platform. The three dimensional printing apparatus forms a plurality of layer objects on the movable platform according to three dimensional model information so as to build a three dimensional object including the layer objects. The method for detecting printing anomaly includes following steps. At least one object image is captured according to at least one view angle by using the image sensor module. At least one checking image associated with the layer objects is obtained according to the three dimensional model information and the view angle. Whether the object image and the checking image are matched to each other or not is determined through comparing the object image and the checking image.

21 Claims, 7 Drawing Sheets

(51) Int. Cl.
*G03G 15/22* (2006.01)
*B33Y 30/00* (2015.01)
*B33Y 10/00* (2015.01)
*G05B 19/4099* (2006.01)

(52) U.S. Cl.
CPC ............ *B33Y 50/02* (2014.12); *G03G 15/224* (2013.01); *G05B 19/4099* (2013.01); *G05B 2219/49023* (2013.01)

(58) Field of Classification Search
CPC .. G01N 21/8851; G03G 15/224; G05B 15/02; G05B 2219/49023; G06F 17/50
See application file for complete search history.

(56) References Cited

U.S. PATENT DOCUMENTS

| | | | |
|---|---|---|---|
| 8,532,806 B1 | 9/2013 | Masson | |
| 8,666,142 B2* | 3/2014 | Shkolnik | B29C 67/0088 382/154 |
| 8,825,452 B2* | 9/2014 | Shono | G06F 17/50 703/1 |
| 8,848,233 B2* | 9/2014 | Gullentops | B29C 67/0059 347/41 |
| 9,216,543 B1* | 12/2015 | Lisitsin | B29C 67/0066 |
| 9,250,620 B2* | 2/2016 | Kotlus | B22F 3/1055 |
| 2007/0035815 A1* | 2/2007 | Edgar | A61B 5/0064 359/359 |
| 2011/0087350 A1 | 4/2011 | Fogel et al. | |
| 2013/0094716 A1* | 4/2013 | Carpio | G06T 5/50 382/109 |
| 2013/0177972 A1* | 7/2013 | Green | C12M 21/08 435/288.7 |
| 2014/0371895 A1* | 12/2014 | Sadusk | B33Y 10/00 700/98 |
| 2015/0093552 A1* | 4/2015 | Biskop | B29C 67/0059 428/201 |
| 2015/0134096 A1* | 5/2015 | Travers | B29C 67/0074 700/98 |
| 2015/0165683 A1* | 6/2015 | Cheverton | B29C 67/0088 382/141 |
| 2015/0177158 A1* | 6/2015 | Cheverton | G01N 21/8851 700/119 |
| 2015/0197062 A1* | 7/2015 | Shinar | B29C 67/0088 700/98 |
| 2015/0258736 A1* | 9/2015 | Chen | B29C 67/0088 700/98 |
| 2015/0266242 A1* | 9/2015 | Comb | G03G 15/224 264/40.1 |
| 2015/0273767 A1* | 10/2015 | Batchelder | G03G 15/224 264/401 |
| 2016/0078670 A1* | 3/2016 | Wu | G06T 15/205 345/420 |

FOREIGN PATENT DOCUMENTS

| | | | |
|---|---|---|---|
| CN | 105127421 A | * | 12/2015 |
| CN | 105574927 A | * | 5/2016 |
| CN | 105666877 A | * | 6/2016 |
| TW | 200801444 | | 1/2008 |
| TW | 201334984 | | 9/2013 |
| WO | 2013098054 | | 7/2013 |

OTHER PUBLICATIONS

"Office Action of China Counterpart Application", issued on Nov. 28, 2016, p. 1-p. 9.

* cited by examiner

THREE DIMENSIONAL PRINTING APPARATUS AND METHOD FOR DETECTING PRINTING ANOMALY

CROSS-REFERENCE TO RELATED APPLICATION

This application claims the priority benefit of Taiwan application serial no. 103114233, filed on Apr. 18, 2014. The entirety of the above-mentioned patent application is hereby incorporated by reference herein and made a part of this specification.

BACKGROUND

1. Technical Field

The technical field relates to a printing apparatus, and particularly relates to a three-dimensional printing apparatus and a method for detecting a printing anomaly thereof.

2. Description of Related Art

As the technology of the computer-aided manufacturing (CAM) advances, the manufacturers have been developing the technology of three-dimensional printing, which is capable of quickly manufacturing the prototypical design concepts. The technology of three-dimensional printing is actually a general term for a series of rapid prototyping (RP) techniques. The basic principles thereof are generally related to manufacturing in layers and using a rapid prototyping machine to form cross sections of a workpiece on the XY plane through scanning and move the machine intermittently on Z-axis along the thickness of the layers, so as to form the three-dimensional object eventually. The three-dimensional printing technology is not limited by geometric shapes, and the RP techniques are shown to be even more advantageous when the component has a higher complexity. Within a very limited time, the three-dimensional model information designed with the three-dimensional computer-aided design (CAD) software becomes available in reality while the man power and the processing time are significantly saved. The user can not only touch the printed component, but also sense the geometric configuration thereof in reality. Furthermore, the user may test the assemblability of the printed component or even the potential function of the component.

Currently, several ways to form thin cross-sectional layers have been developed. For example, the printing head usually moves on the base along the XY axes in the XYZ coordinate system constructed based on the three-dimensional model information, so as to spray and coat the construction material to form the correct cross-sectional layers. The deposited material may be cured afterwards to form the desired cross-sectional layers and the three-dimensional object may be printed by curing the layers sequentially. However, in the three-dimensional printing process, the three-dimensional object being printed may not be successfully attached to the forming platform and consequently dislocated. Or, the three-dimensional object may hit the printing head due to unevenness of the cross-sections or warpage of the object and is dislocated from the original position. Dislocation of the three-dimensional object may result in failure of three-dimensional printing. Therefore, how to facilitate the speed and quality of three-dimensional printing is still an important issue for artisans of this field.

SUMMARY OF THE INVENTION

Thus, one of the exemplary embodiments provides a three-dimensional printing apparatus capable of detecting whether a three-dimensional object being printed is deformed or dislocated, so as to improve the printing quality of three-dimensional printing.

One of exemplary embodiments provides a three-dimensional printing apparatus, including a movable platform, a printing unit, an image sensor module, and a control unit. The movable platform includes a carrying surface, and the printing unit is disposed above the platform. The image sensor module is disposed above the platform. In addition, the control unit is coupled with the movable platform, the printing unit, and the image sensor module. The control unit controls the printing unit based on three-dimensional model information, so as to form the plurality of layer objects on the carrying surface to constitute the three-dimensional object including the layer objects. In addition, the control unit uses the image sensor module to capture at least one object image of the three-dimensional object from at least one view angle, and further obtains at least one checking image associated with layer objects based on the three-dimensional model information and the at least one view angle. Moreover, the control unit checks whether the object image matches the checking image by comparing the object and checking images.

From another perspective, one of exemplary embodiments provides a method for detecting a printing anomaly adapted for a three-dimensional printing apparatus including a image sensor module and a movable platform. The three-dimensional printing apparatus forms a plurality of layer objects on a carrying surface of the movable platform based on three-dimensional model information to constitute a three-dimensional object including the layer objects. The method for detecting the printing anomaly includes steps as follows. The image sensor module is used to capture at least one object image of the three-dimensional object from at least one view angle. At least one checking image associated with the layer objects is obtained based on the three-dimensional model information and the at least one view angle. Whether the object image matches the checking image is determined by comparing the at least one object image and the at least one checking image.

Based on the above, the three-dimensional printing apparatus according to the embodiments of the disclosure may detect whether the three-dimensional object is deformed or dislocated by comparing the object image captured by the image sensor module with the checking image produced based on the three-dimensional model information when printing the three-dimensional object. When the three-dimensional object being printed hits the printing head and is dislocated, the three-dimensional printing apparatus may detect the anomaly of the three-dimensional object and warn the user accordingly during printing. In this way, the user may perform a subsequent operation based on the warning of the three-dimensional printing apparatus, so as not to continue printing when the three-dimensional object is dislocated or deformed. Thus, the exemplary embodiments certainly improve the usefulness of the three-dimensional printing apparatus in the actual practice and in an operation, and the manufacture cost may be further reduced.

In order to make the aforementioned and other features and advantages of the disclosure comprehensible, several exemplary embodiments accompanied with figures are described in detail below.

BRIEF DESCRIPTION OF THE DRAWINGS

The accompanying drawings are included to provide a further understanding of the disclosure, and are incorporated in and constitute a part of this specification. The drawings illustrate embodiments of the disclosure and, together with the description, serve to explain the principles of the disclosure.

DESCRIPTION OF THE EMBODIMENTS

Reference will now be made in detail to the present preferred embodiments of the disclosure, examples of which are illustrated in the accompanying drawings. Wherever possible, the same reference numbers are used in the drawings and the description to refer to the same or like parts.

It is to be understood that both the foregoing and other detailed descriptions, features, and advantages are intended to be described more comprehensively by providing embodiments accompanied with figures hereinafter. In the following embodiments, wordings used to indicate directions, such as "up," "down," "front," "back," "left," and "right", merely refer to directions in the accompanying drawings. Therefore, the directional wording is used to illustrate rather than limit the disclosure. In addition, in the following embodiments, the same or similar elements are referred to by the same or similar reference symbols.

Figure 1:
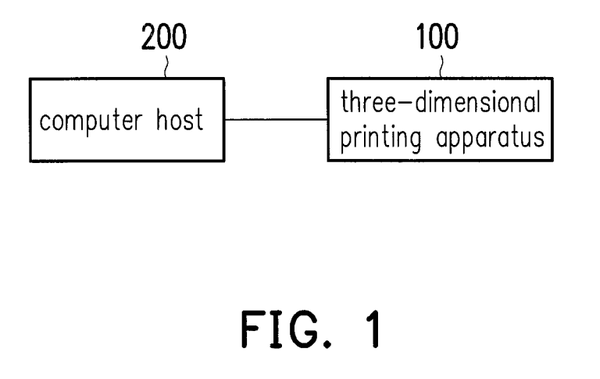
FIG. 1 is a block diagram illustrating how a three-dimensional printing apparatus works according to an exemplary embodiment.

FIG. 1 is a block diagram illustrating how a three-dimensional printing apparatus works according to an exemplary embodiment. Referring to FIG. 1, a three-dimensional printing apparatus 100 of this embodiment is suitable for printing a three-dimensional object according to three-dimensional model information. More specifically, a computer host 200 is an apparatus having a computing function, such as a computer apparatus like a laptop computer, a tablet computer, or a desktop computer. The disclosure does not intend to impose a limitation on the types of the computer host 200. The computer host 200 may edit and process a three-dimensional model of a three-dimensional object and transmit relevant three-dimensional model information to the three-dimensional printing apparatus 100, such that the three-dimensional printing apparatus 100 may print the three-dimensional object according to the three-dimensional model information. In this embodiment, the three-dimensional model information may be a three-dimensional digital image file that may be constructed with the computer host 200 using a computer-aided design (CAD) or animation modeling software. In addition, the digital three-dimensional model information is sectioned into a plurality of cross section information, such that the three-dimensional printing apparatus 100 may sequentially obtain a plurality of layer objects based on the cross section information of the digital three-dimensional model information. The layer objects are stacked to form the three-dimensional object.

Figure 2:
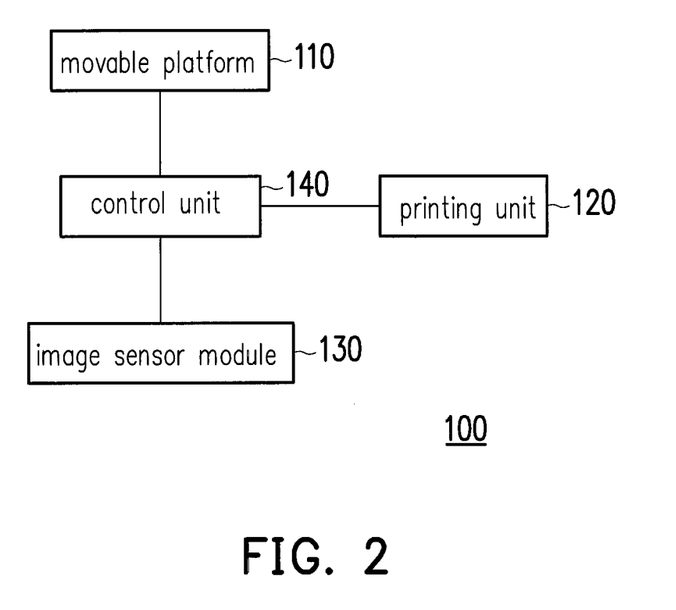
FIG. 2 is a schematic block diagram illustrating a three-dimensional printing apparatus according to an exemplary embodiment.

FIG. 2 is a schematic block diagram illustrating a three-dimensional printing apparatus according to an exemplary embodiment. Referring to FIG. 2, the three-dimensional printing apparatus 100 includes a movable platform 110, a printing unit 120, an image sensor module 130, and a control unit 140. Functions of the components are respectively described below.

The movable platform 110 includes a carrying surface that bears the three-dimensional object being printed. The printing unit 120 is movably disposed above the movable platform 110, so as to coat a forming material on the carrying surface of the movable platform 110. The image sensor module 130 is disposed above the movable platform 110, and is, for example, an optical scanning apparatus or an image capturing apparatus configured to capture an image of the three-dimensional object on the movable platform 110. For example, the image sensor module may be an optical scanning apparatus such as a contact image sensor (CIS), and may be an image capturing apparatus such as a complementary metal oxide semiconductor (CMOS) image sensor or a charged coupled device (CCD) image sensor. The disclosure does not intend to limit the configuration of the image sensor module in practice. Any image sensor module capable of capturing an image of the three-dimensional object on the movable platform by taking a picture or scanning fall within the scope claimed in the disclosure.

In addition, the control unit 140 is coupled with the movable platform 110, the printing unit 120, and the image sensor module 130 to read the three-dimensional model information and control, based on the three-dimensional model information, an operation of the three-dimensional printing apparatus 100 as a whole to print the three-dimensional object. For example, the control unit 140 may control a moving path of the printing unit 120 based on the three-dimensional digital model information. The control unit 140 is, for example, an element having a computing function, such as a central processing unit, a chip set, a microprocessor, an embedded controller, etc. The disclosure is not limited thereto. Specifically speaking, the control unit 140 controls the printing unit 120 based on the three-dimensional model information, so as to form the plurality of layer objects on the carrying surface of the movable platform 110 to constitute the three-dimensional object including the layer objects.

It should be noted that based on different three-dimensional object forming principles, the printing unit 120 may be configured differently in the actual practice. The disclosure is not limited thereto. For example, when the three-dimensional printing apparatus 100 is a fused deposition modeling (FDM) three-dimensional printing apparatus, the printing unit 120 is, for example, a printing head to heat and fuse the forming material, and the forming material may be a thermal fusible material. The printing unit 120 may heat the forming material, so as to fuse the forming material supplied to the printing unit 120 into a liquid material in a fused state. The fused forming material at a high temperature is then squeezed out by the printing unit 120. Therefore, the fused forming material may be cured on the carrying surface in a layer-by-layer manner to construct the three-dimensional object.

In addition, when the three-dimensional printing apparatus is a material-jetting three-dimensional printing apparatus, the printing unit 120 is, for example, a nozzle that sprays and coats the forming material. At this time, the forming material to be deposited may be a photosensitive resin in a liquid or slurry state. The printing unit 120 then directly sprays the forming material on the carrying surface of the platform and then the forming material is cured naturally or by a specific light source, so as to form a desired cross-sectional layer. Therefore, the photosensitive resin in the liquid or slurry state may be cured on the carrying surface in the layer-by-layer manner to form the three-dimensional object. It should be noted in particular that although the three-dimensional printing apparatus 100 is described by taking the FDM and material jetting three-dimensional printing apparatuses as examples, the disclosure is not limited thereto. Any three-dimensional printing apparatuses that coat the forming material on the movable platform 110 by using the printing unit 120 fall within the scope claimed in the disclosure.

Figure 3:
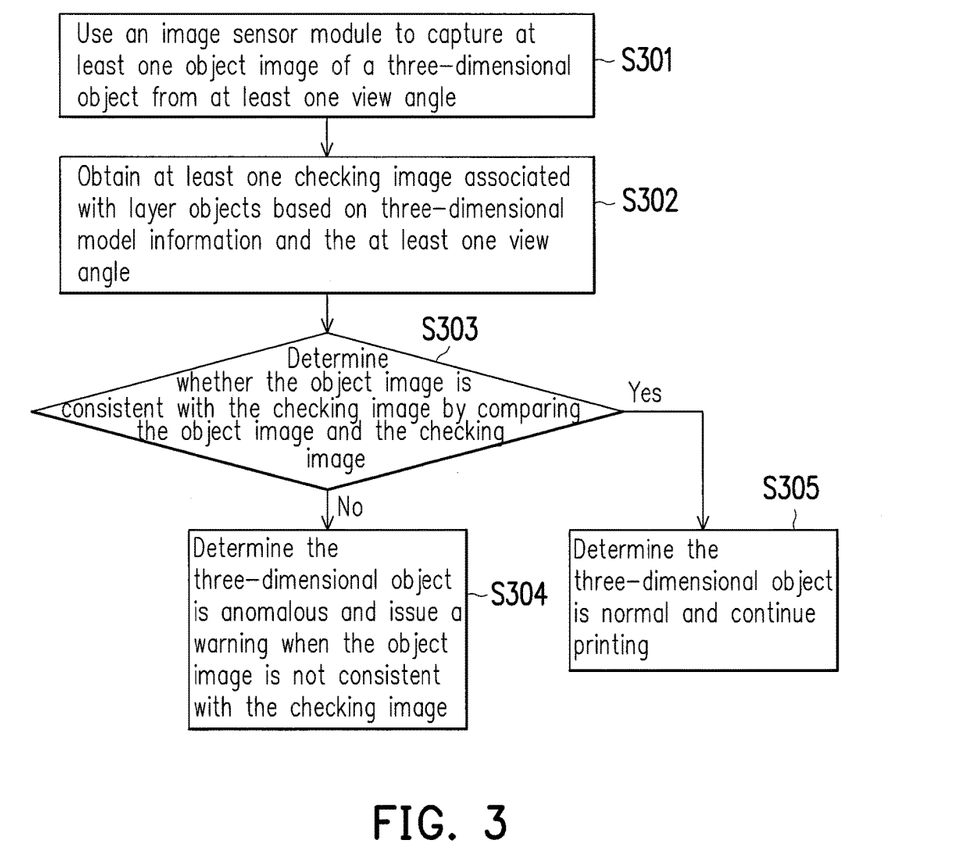
FIG. 3 is a flowchart illustrating a method for detecting a printing anomaly according to an exemplary embodiment.

FIG. 3 is a flowchart illustrating a method for detecting a printing anomaly according to an exemplary embodiment. The method for detecting the printing anomaly of this embodiment is suitable for the three-dimensional printing apparatus 100 shown in FIG. 2. In the following, with reference to FIGS. 2 and 3 simultaneously, the components and modules in the three-dimensional printing apparatus 100 are used to describe steps of this embodiment in detail.

First of all, at Step S301, the control unit 140 uses the image sensor module 130 to capture at least one object image of the three-dimensional object from at least one view angle. Specifically speaking, based on the position where the image sensor module 130 is disposed, the image sensor module 130 may capture at least one object image of the three-dimensional object on the movable platform 110 from the at least one view angle with respect to the position where the image sensor module 130 is disposed. Namely, the object image reveals an actual forming state of the three-dimensional object being printed on the movable platform 110. In addition, the image sensor module 130 may obtain different object images from different view angles (e.g. from a top view angle or a side view angle).

At Step S302, the control unit 140 obtains at least one checking image associated with the layer object based on the at least one view angle and the three-dimensional model information. Specifically, the three-dimensional printing apparatus 100 prints the three-dimensional object based on the three-dimensional model information transmitted from the computer host 200. Therefore, the three-dimensional object actually printed by the three-dimensional printing apparatus 100 is the same as the three-dimensional model in the three-dimensional model information. Therefore, in the exemplary embodiment, the control unit 140 generates the checking image showing an ideal state based on the three-dimensional model information, and the checking image may be used to check whether the three-dimensional object being printed is deformed or dislocated. Similarly, the checking images may correspondingly show different parts of the three-dimensional object when the view angles are different. It should be noted in particular that to compare the ideal checking image and the actual object image, the checking image and the object image that are compared to each other should be from the same view angle with respect to the three-dimensional object.

Then, at Step S303, the control unit 140 checks whether the object image matches the checking image by comparing the object and checking images. If the three-dimensional object being printed is not dislocated or deformed, the checking image produced based on the three-dimensional model information may be similar to or the same as the object image taken in the actual situation. Therefore, when the object image does not match the checking image (the determination result is "No" in Step S303), the control unit 140 determines that the three-dimensional object is anomalous and issues a warning at Step S304. When the object image matches the checking image (the determination result is "Yes" in Step S303), the control unit 140 controls the printing unit 120 to continue printing the three-dimensional object at Step S305.

According to the above, it can be known that the image sensor module 130 may take or capture different object images from different view angles, and the view angle at which the image sensor module 130 takes/captures an image is determined based on how the image sensor module 130 is configured or where the image sensor module 130 is disposed. In addition, to display the checking and object images of the same part of the three-dimensional object, the checking image is produced based on the view angle of the object image. For example, the image sensor module 130 may be disposed right above the movable platform 110 and takes an image of the three-dimensional object on the movable platform 110 below, so as to obtain a top view of the three-dimensional object. In addition, the image sensor module 130 may be disposed on one side above the movable platform 110, and takes an image of the three-dimensional object on the movable platform 110 from a side view angle parallel to the carrying surface, so as to obtain a side view of the three-dimensional object.

Figure 4:
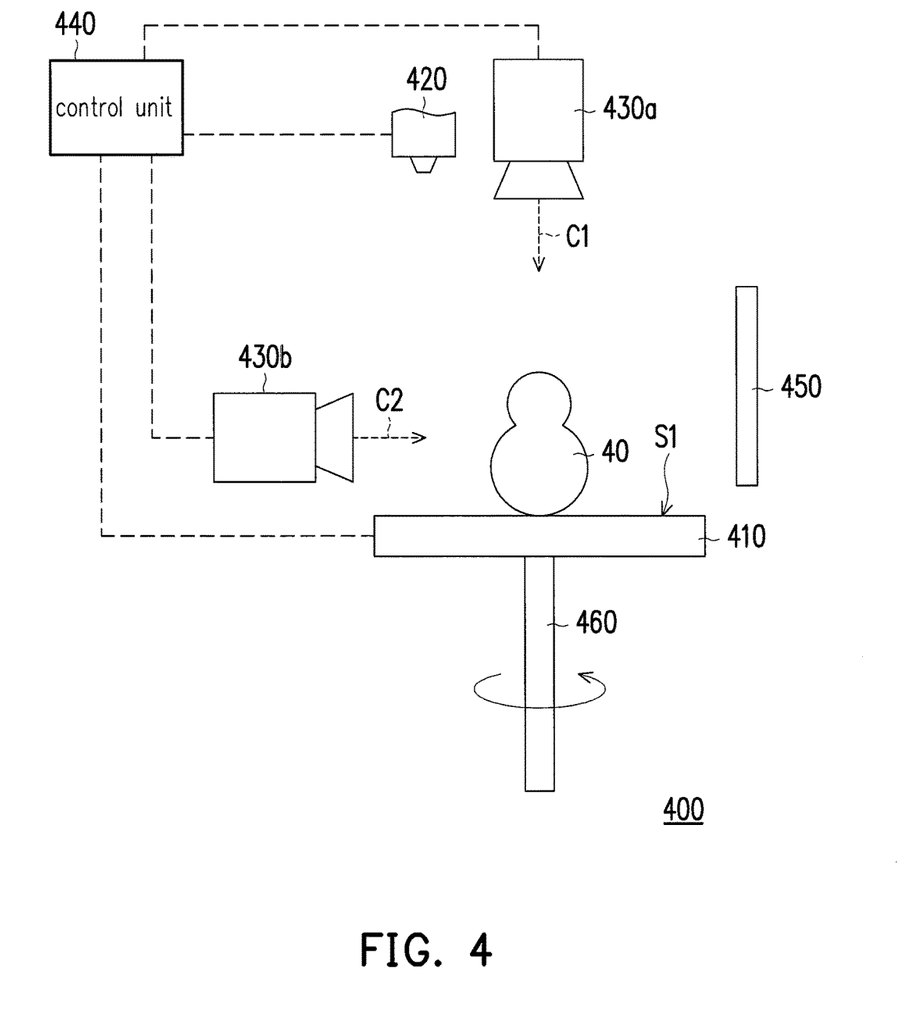
FIG. 4 is a schematic diagram of a three-dimensional printing apparatus according to an exemplary embodiment.

To further describe details of the exemplary embodiment, FIG. 4, which is a schematic diagram of a three-dimensional printing apparatus according to an exemplary embodiment, is provided. Referring to FIG. 4, a three-dimensional printing apparatus 400 of this embodiment is described with a FDM three-dimensional printing apparatus. However, the disclosure is not limited thereto. The three-dimensional printing apparatus 400 includes a movable platform 410, a printing head 420, an image sensor module 430a, an image sensor module 430b, a control unit 440, and a screen 450. Here, a Cartesian coordinate system is provided herein for the convenience of describing relevant components and movements thereof.

The movable platform 410 includes a carrying surface S1. The printing head 420 is disposed above the movable platform 410. The printing head 420 is configured to move along the XY plane and along the normal direction of the XY plane (i.e. along Z-axis), so as to print each of the layer objects on the carrying surface S1 in the layer-by-layer manner to gradually form a three-dimensional object 40. In other words, the control unit 440 receives the three-dimensional model information from the computer host, and controls the components of the three-dimensional printing apparatus 400 accordingly to print the plurality of layer objects. Based on the above, the three-dimensional object printed by the three-dimensional printing apparatus 400 may be considered as being formed by the plurality of layer objects, and each of the layer objects correspondingly has a cross section due to the shape of the three-dimensional object.

In addition, in this embodiment, the image sensor modules 430a and 430b are video cameras or photographic cameras. The image sensor module 430a is disposed above the movable platform 410, so as to take an image toward the movable platform 410 to obtain a top view of the three-dimensional object 40. The image sensor module 430a may be disposed at the top part of the three-dimensional printing apparatus 400. In an embodiment, the image sensor module 430a may be disposed on the printing head 420 and moves the image sensor module 430*a* to a height and position suitable to take the object image by controlling the printing head 420.

Thus, the image sensor module 430*a* takes the object image toward the carrying surface S1 in a capturing direction C1. In addition, the capturing direction C1 and the carrying surface S1 are perpendicular to each other. It should be noted that the object images taken by the image sensor module 430*a* are from the same view angle (i.e. the top view angle), and the object images taken by the image sensor module 430*a* display a top part of the three-dimensional object 40. Therefore, since the image sensor module 430*a* takes the object image from the top view angle, the control unit 440 converts the three-dimensional model information to obtain a plurality of cross-sectional views in which each of the layer objects is projected onto the carrying surface S1. In addition, the control unit 440 stacks the cross-sectional views to obtain a checking view corresponding to a view angle.

Specifically speaking, in this embodiment, the control unit 440 controls a moving path of the printing head 420 on the XY plane using a control code (e.g. G code). Namely, the control code includes information relevant to the cross-sectional view of the layer object. Therefore, the control unit 440 may generate the cross-sectional view of each of the layer objects based on the control code, and produce the checking image by stacking the cross-sectional views that are already printed.

Then, the control unit 440 determines whether the object image and the checking image are matched by comparing the object image taken in the actual situation and the ideal checking image, so as to determine whether the three-dimensional object 40 is anomalous, such as being dislocated or deformed. It should be noted that before the control unit 440 compares the object image taken by the image sensor module 430*a* and the checking image, the control unit 440 may scale the object image based on the height at which the image sensor module 430 takes the image.

Figure 5:
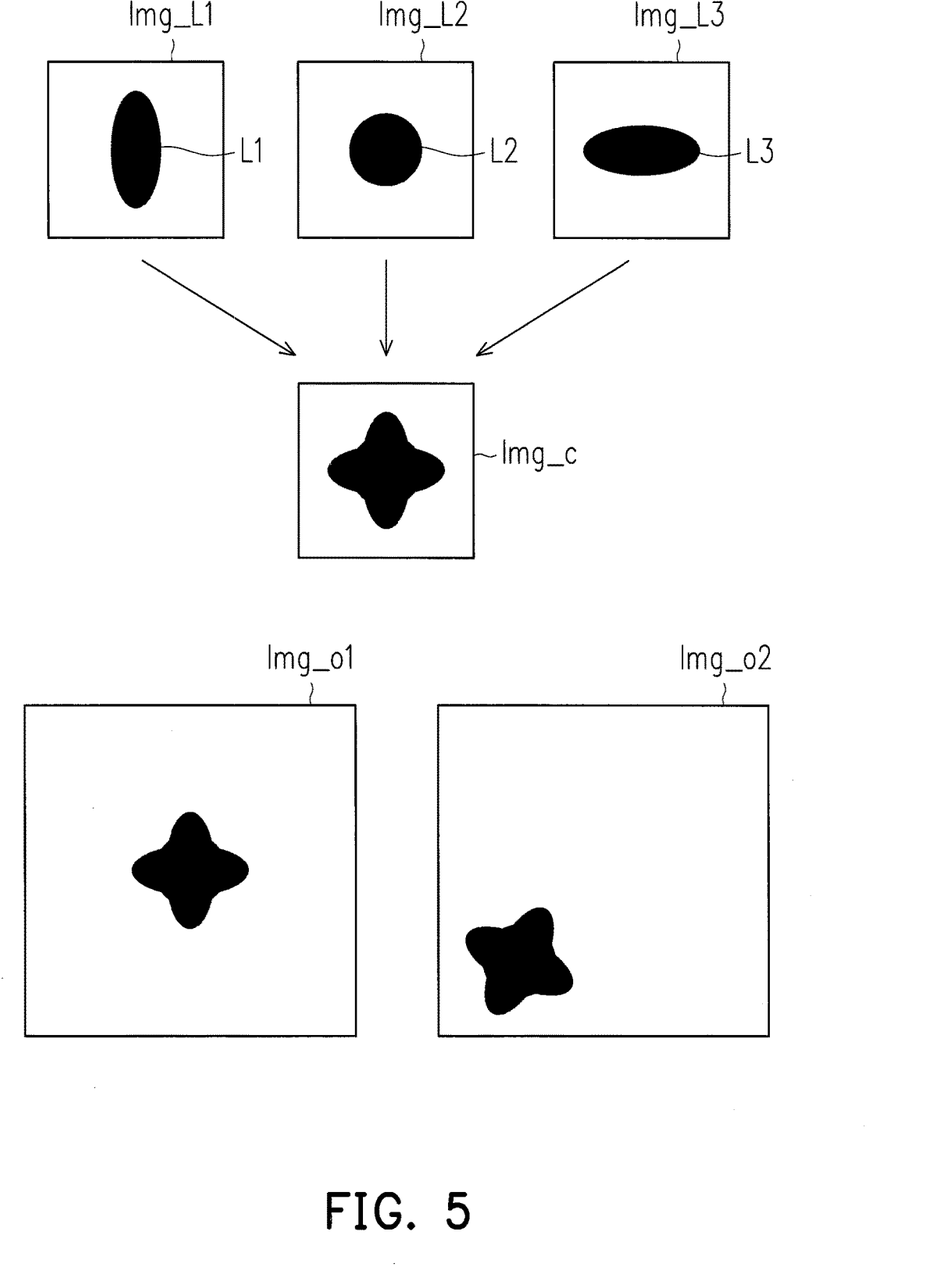
FIG. 5 is an exemplary diagram of a checking image and an object image according to an exemplary embodiment.

To describe how to produce the checking image from top view angle in detail, FIG. 5, an exemplary diagram illustrating a checking image and an object image according to an exemplary embodiment, is provided. In the example shown in FIG. 5, the control unit 440 may switch G codes of layer objects L1 to L3 to generate cross-sectional views Img_L1 to Img_L3 corresponding to the top view angle. Then, the control unit 440 stacks and combines the cross-sectional views Img_L1 to Img_L3 to obtain a checking image Img_c corresponding to the top view angle. Thus, given that an object image Img_o1 is an image taken by the image sensor module 430*a*, since the object image Img_o1 matches the checking image Img_c, the three-dimensional object is not anomalous. However, assuming an object image Img_o2 is an image taken by the image sensor module 430*a*, since the object image Img_o2 does not match the checking image Img_c, the three-dimensional object is anomalous.

It should be noted that in an embodiment, the control unit 440 may compare profile or position information of the object image and the checking image to determine whether the object image matches the checking image. In addition, the profile information relate to profiles of the three-dimensional object in the object image and the checking image, and the position information relates to positions of the three-dimensional object in the object image and in the checking image. Specifically, the control unit 440 compares whether the profile information of the object image is consistent with the profile information of the checking image and compares whether the object position of the object image is consistent with the object position of the checking image, thereby determining whether the object image matches the checking image. The object image Img_o2 in the example shown in FIG. 5 is taken as an example. Although profile information of the object image Img_o2 is consistent with the profile information of the checking image, position information of the object image Img_o2 is not consistent with the position information of the checking image. Therefore, it is determined that the three-dimensional object on the movable platform 410 is dislocated.

Besides, the image sensor module 430*b* is disposed at one side of the movable platform 410. The screen 450 is disposed on the other side of the movable platform 410 opposite to the image sensor module 430*b*. The image sensor module 430*b* captures the object image toward the screen 450 in a capturing direction C2. The capturing direction C2 is parallel with the carrying surface S1. In addition, in this embodiment, the movable platform 410 is configured to rotate along a rotation axis 460. Therefore, the image sensor module 430*b* may capture a plurality of different object images from a plurality of different side view angles by rotating the movable platform 410. In other words, the image sensor module 430*b* may capture a plurality of object images from different side view angles by taking the images surroundingly.

In addition, the control unit 440 may produce checking images corresponding to different side view angles based on the three-dimensional model information associated with each of the layer objects. Thus, the control unit 440 compares the plurality of object images captured by the image sensor module 430*b* with the plurality of checking images produced based on the three-dimensional model information, and determines whether the three-dimensional object being printed is anomalous based on an outcome of comparison. It should be noted that the disclosure does not intend to limit the number of the object images captured by the image sensor module 430*b*. Namely, the angles and number of the side view angles corresponding to each of the object images may be determined based on the needs in the actual practice.

Figure 6:
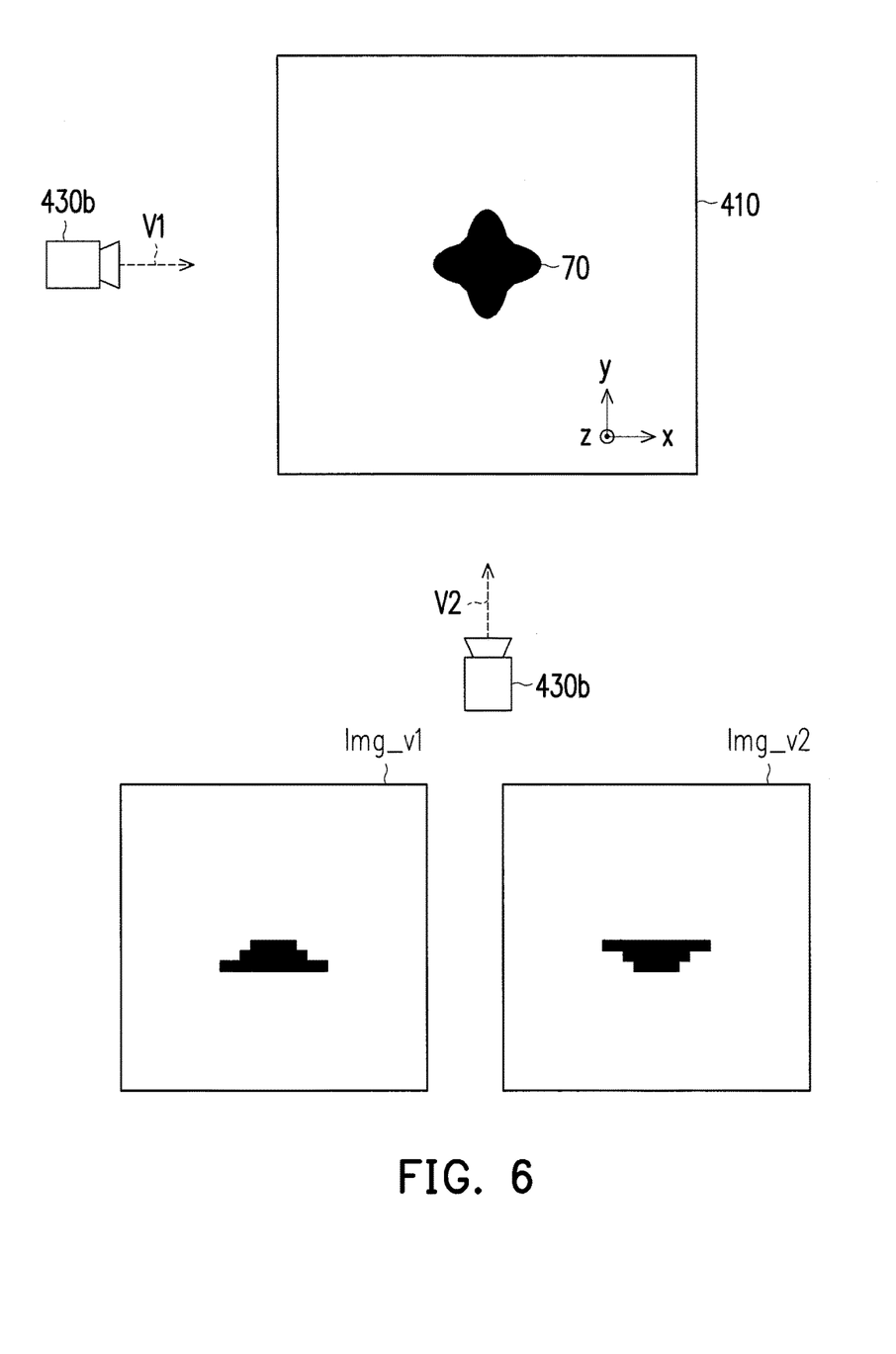
FIG. 6 is an exemplary diagram of an object image according to an exemplary embodiment.
Figure 7:
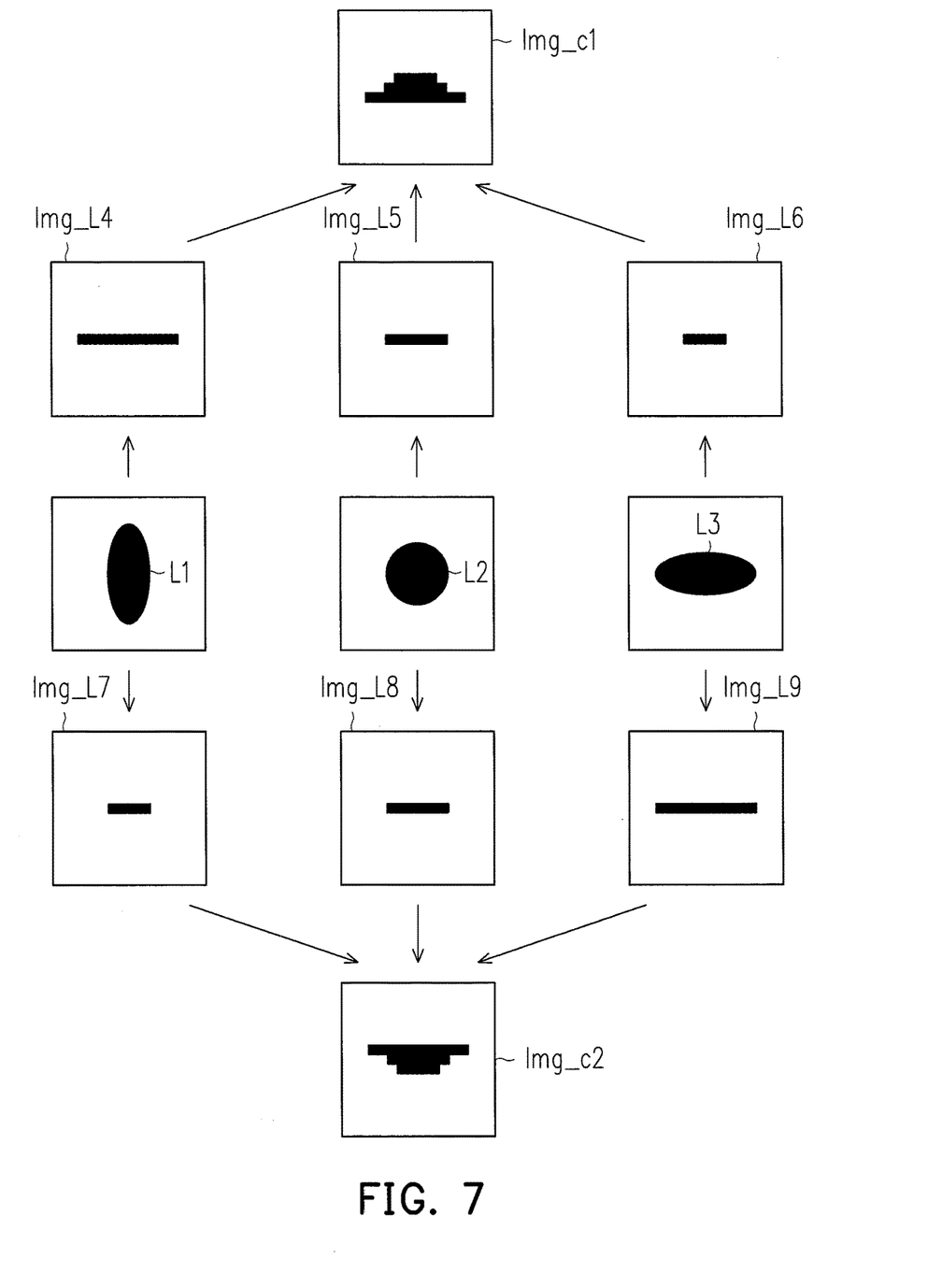
FIG. 7 is an exemplary diagram of a checking image according to an exemplary embodiment.

To describe how to produce a checking image from the side view angle in detail, FIG. 6 is an exemplary diagram of an object image according to an exemplary embodiment. FIG. 7 is an exemplary diagram of a checking image according to an exemplary embodiment. Referring to FIG. 6, in this embodiment, the control unit 440 controls the movable platform 410 to rotate, so as to use the image sensor module 430*b* to capture a first object image Img_v1 and a second object image Img_v2 from a first side view angle V1 and a second side view angle V2.

To compare the object image and the checking image corresponding to the same side view angle (e.g. the first side view angle V1 and the second side view angle V2), the control unit 440 may convert the three-dimensional model information based on the first side view angle V1 and the second side view angle V2. Specifically, referring to FIG. 7, the control unit 440 may convert three-dimensional model information of a three-dimensional object 70 based on the first side view angle V1, so as to obtain a plurality of first object width views Img_L4 to Img_L6 of each of the layer objects L1 to L3 of the three-dimensional object 70 according to the first side view angle V1. For example, the control unit 440 may obtain the first object width view Img_L4 of the layer object L1 based on the three-dimensional model information relevant to the layer object L1.

Also, the control unit 440 may convert the three-dimensional model information of the three-dimensional object 70 based on the second side view angle V2, so as to obtain a plurality of second object width views Img_L7 to Img_L9 of each of the layer objects L1 to L3 of the three-dimensional object 70 according to the second side view angle V2. For example, the control unit 440 may obtain the second object width view Img_L8 of the layer object L2 based on the three-dimensional model information relevant to the layer object L2.

Thus, the control unit 440 combines the first object width views Img_L4 to Img_L6 to obtain a first checking image Img_c1 corresponding to the first side view angle V1. The control unit 440 combines the second object width views Img_L7 to Img_L9 to obtain a second checking image Img_c2 corresponding to the second side view angle V2. Also, the control unit 440 combines the first object width views Img_L4 to Img_L6 and the second object width views Img_L7 to Img_L9 based on an order that the layer objects L1 to L3 are stacked on the movable platform 440.

Referring to FIGS. 6 and 7 simultaneously, the control unit 440 compares the first object image Img_v1 and the first checking image Img_c1 from the first side view angle V1 to determine whether the first object image Img_v1 and the first checking image Img_c1 corresponding to the first view angle V1 are matched. In addition, the control unit 440 compares the second object image Img_v2 and the second checking image Img_c2 to determine whether the second object image Img_v2 and the second checking image Img_c2 corresponding to the second view angle V2 are matched. If the first object image Img_v1 and the first checking image Img_c1 are matched and the second object image Img_v2 and the second checking image Img_c2 are matched, the control unit 440 determines that the three-dimensional object 70 is not anomalous.

Figure 8:
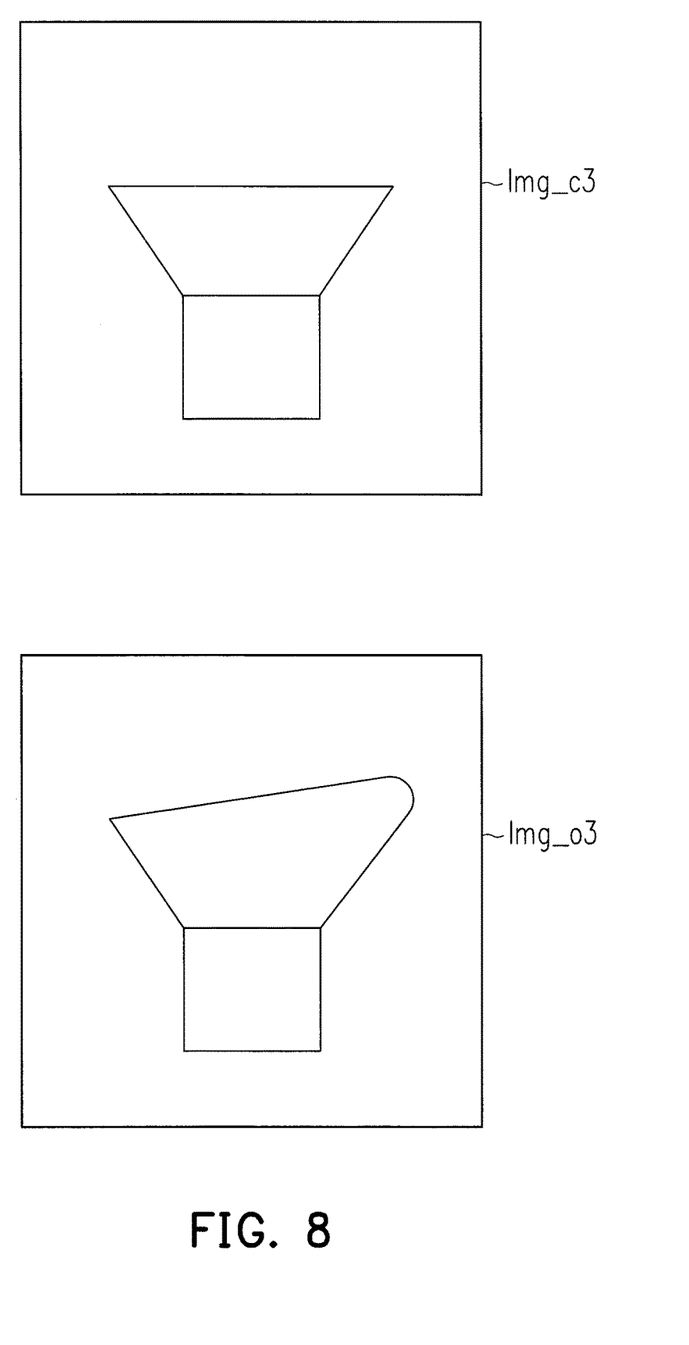
FIG. 8 is a schematic diagram illustrating a scenario in which a printing anomaly occurs according to an exemplary embodiment.

However, if the first object image Img_v1 and the first checking image Img_c1 are not matched and/or the second object image Img_v2 and the second checking image Img_c2 are not matched, the control unit 440 determines the three-dimensional object 70 has an anomaly such as being warped, dislocated, or deformed. Taking warpage of the three-dimensional object as an example, FIG. 8 is a schematic diagram illustrating a scenario in which a printing anomaly occurs according to an exemplary embodiment. Referring to FIG. 8, given that an image produced by the control unit 440 based on the three-dimensional modeling information is a checking image Img_c3, and contents displayed in the checking image Img_c3 represent a state where the three-dimensional object is normally printed. As shown in FIG. 8, since an object image Img_o3 captured by the image sensor module 430b does not match the checking image Img_c3, the control unit 440 determines the three-dimensional object is anomalous and issues a warning to remind the user or directly terminates the printing process.

It should be noted that although the embodiment shown in FIG. 4 is described by using a FDM three-dimensional printing apparatus including the image sensor modules 430a and 430b as an example, the disclosure is not limited thereto. If the three-dimensional printing apparatus is a material jetting three-dimensional printing apparatus, since the three-dimensional object being printed is encapsulated in a support material, the material-jetting three-dimensional printing apparatus is not able to capture the image that displays the actual state of the three-dimensional object from the side view angle parallel to the carrying surface. In addition, the object image captured from the top view angle perpendicular to the carrying surface only displays a cross-sectional profile of the topmost layer object. Thus, for the material-jetting three-dimensional printing apparatus, the image sensor module disposed right above the platform may be used to capture the object image of the three-dimensional object, so as to compare the object image with the cross-sectional view of the topmost layer object and thus determine whether the three-dimensional object is anomalous. The image sensor module disposed in the material-jetting three-dimensional printing apparatus is a camera disposed at the top part of the three-dimensional printing apparatus or an optical scanning apparatus disposed at the nozzle, for example. The disclosure is not limited thereto.

In view of the foregoing, in the embodiments of the disclosure, the three-dimensional printing apparatus may capture the object image of the three-dimensional object from a specific view angle during printing. Therefore, the three-dimensional printing apparatus may compare the object image with the checking image produced based on the three-dimensional model information to detect whether the three-dimensional object is anomalous such as being dislocated or deformed. When the three-dimensional printing apparatus detects that the three-dimensional object is anomalous, the three-dimensional printing apparatus issues a warning to the user or directly terminates the printing process accordingly. In this way, the three-dimensional printing apparatus is prevented from printing in a anomalous state, thereby preventing waste of the printing material and time and improving the printing quality of the three-dimensional printing apparatus.

It will be apparent to those skilled in the art that various modifications and variations can be made to the structure of the present disclosure without departing from the scope or spirit of the disclosure. In view of the foregoing, it is intended that the present disclosure cover modifications and variations of this disclosure provided they fall within the scope of the following claims and their equivalents.

What is claimed is:

1. A three-dimensional printing apparatus, comprising:
a movable platform, comprising a carrying surface;
a printing unit, disposed above the movable platform and forming at least one layer object on the carrying surface based on a three-dimensional model information;
an image sensor module, disposed above the movable platform to capture an object image of the at least one layer object in a capturing direction; and
a control unit, coupled with the printing unit and the image sensor module, wherein the control unit determines a checking image based on the three-dimensional model information and the capturing direction and compares the object image with the checking image,
wherein the operation that the control unit compares the object image with the checking image comprises: comparing profile information of the object image with profile information of the checking image.

2. The three-dimensional printing apparatus as claimed in claim 1, wherein when the object image does not match the checking image, the control unit determines the three-dimensional object is anomalous and issues a warning.

3. The three-dimensional printing apparatus as claimed in claim 1, wherein when the object image does not match the checking image, the control unit determines that the three-dimensional object is anomalous and terminates a printing process.

4. The three-dimensional printing apparatus as claimed in claim 1, wherein the capturing direction is perpendicular to the carrying surface.

5. The three-dimensional printing apparatus as claimed in claim 4, wherein when the printing unit forms the at least one layer object on the carrying surface based on the three-dimensional model information, the control unit coverts the three-dimensional model information to obtain a plurality of cross-sectional views of each of the layer object projected on the carrying surface, and the control unit stacks the cross-sectional views to determine the checking image.

6. The three-dimensional printing apparatus as claimed in claim 1, wherein the image sensor module is disposed at one side of the movable platform, the three-dimensional printing apparatus further comprises a screen, the screen is disposed at the other side of the movable platform opposite to the image sensor module, the capturing direction of the image sensor module is toward the screen, and the capturing direction is parallel to the carrying surface.

7. The three-dimensional printing apparatus as claimed in claim 6, wherein the movable platform is disposed to rotate along a rotation axis.

8. The three-dimensional printing apparatus as claimed in claim 1, wherein the operation that the control unit compares the object image with the checking image further comprises: comparing an object position of the object image with an object position of the checking image.

9. A method for detecting a printing anomaly adapted for a three-dimensional printing apparatus comprising an image sensor module and a movable platform, wherein the three-dimensional printing apparatus forms a plurality of layer objects on a carrying surface of the movable platform based on three-dimensional model information to constitute a three-dimensional object comprising the layer objects, the method for detecting the printing anomaly comprising:
   using the image sensor module to capture at least one object image of the three-dimensional object from at least one view angle;
   obtaining at least one checking image associated with the layer objects based on the three-dimensional model information and the at least one view angle; and
   determining whether the at least one object image match the at least one checking image by comparing the at least one object image and the at least one checking image,
   wherein the step of determining whether the at least one object image match the at least one checking image by comparing the at least one object image and the at least one checking image comprises: comparing profile information of the object image with profile information of the checking image.

10. The method for detecting the printing anomaly as claimed in claim 9, further comprising:
   determining the three-dimensional object is anomalous and issuing a warning, when the at least one object image does not match the at least one checking image.

11. The method for detecting the printing anomaly as claimed in claim 9, wherein the image sensor module captures the at least one object image toward the carrying surface along an axial direction, and the axial direction is perpendicular to the carrying surface.

12. The method for detecting the printing anomaly as claimed in claim 11, wherein the step of obtaining the at least one checking image associated with the layer objects based on the three-dimensional model information and the at least one view angle comprises:
   converting the three-dimensional model information to obtain a plurality of cross-sectional views of each of the layer objects projected on the carrying surface; and
   stacking the cross-sectional views to obtain the at least one checking image corresponding to the at least one view angle.

13. The method for detecting the printing anomaly as claimed in claim 9, wherein the image sensor module is disposed at one side of the movable platform, the three-dimensional printing apparatus further comprises a screen disposed at the other side of the movable platform opposite to the image sensor module, and the image sensor module captures the at least one object image toward the screen in a capturing direction, the capturing direction being parallel to the carrying surface.

14. The method for detecting the printing anomaly as claimed in claim 13, wherein the movable platform is configured to rotate along a rotation axis, the at least one view angle comprises a first view angle and a second view angle, and the step of using the image sensor module to capture the at least one object image of the three-dimensional object from the at least one view angle comprises:
   controlling the movable platform to rotate, so as to use the image sensor module to capture a first object image and a second object image of the at least one object image of the three-dimensional object from the first view angle and the second view angle.

15. The method for detecting the printing anomaly as claimed in claim 14, wherein the step of obtaining the at least one checking image associated with the layer objects based on the three-dimensional model information and the at least one view angle comprises:
   respectively converting the three-dimensional model information based on the first view angle and the second view angle, so as to obtain a plurality of first object width views of each of the layer objects from the first view angle and a plurality of second object width views of each of the layer objects from the second view angle; and
   respectively combining the first object width views and the second object width views to obtain a first checking image and a second checking image of the at least one checking image.

16. The method for detecting the printing anomaly as claimed in claim 15, wherein the step of determining whether the at least one object image matches the at least one checking image by comparing the at least one object image and the at least one checking image comprises:
   comparing the first object image and the first checking image to determine whether the first object image from the first view angle matches the first checking image corresponding to the first view angle; and
   comparing the second object image and the second checking image to determine whether the second object image from the second view angle matches the second checking image corresponding to the second view angle.

17. The method for detecting the printing anomaly as claimed in claim 9, wherein the step of determining whether the at least one object image matches the at least one checking image by comparing the at least one object image and the at least one checking image comprises:
   comparing to determine whether the profile information of the at least one object image is consistent with the profile information of the at least one checking image; and
   comparing to determine whether an object position of the at least one object image is consistent with an object position of the at least one checking image, wherein the at least one object image does not match the at least one checking image when the profile information of the at least one object age is not consistent with the profile information of the at least one checking image or the object position of the at least one object image is not consistent with the object position of the at least one checking image.

18. A three-dimensional printing apparatus, comprising:
a movable platform, comprising a carrying surface;
a printing unit, disposed above the movable platform and forming at least one layer object on the carrying surface based on a three-dimensional model information;
an image sensor module, disposed above the movable platform to capture an object image of the at least one layer object in a capturing direction; and
a control unit, coupled with the printing unit and the image sensor module, wherein the control unit determines a checking image based on the three-dimensional model information and the capturing direction and compares the object image with the checking image,
wherein the capturing direction is perpendicular to the carrying surface,
wherein when the printing unit forms the at least one layer object on the carrying surface based on the three-dimensional model information, the control unit coverts the three-dimensional model information to obtain a plurality of cross-sectional views of each of the layer object projected on the carrying surface, and the control unit stacks the cross-sectional views to determine the checking image.

19. A method for detecting a printing anomaly adapted for a three-dimensional printing apparatus comprising an image sensor module and a movable platform, wherein the three-dimensional printing apparatus forms a plurality of layer objects on a carrying surface of the movable platform based on three-dimensional model information to constitute a three-dimensional object comprising the layer objects, the method for detecting the printing anomaly comprising:
using the image sensor module to capture at least one object image of the three-dimensional object from at least one view angle;
obtaining at least one checking image associated with the layer objects based on the three-dimensional model information and the at least one view angle; and
determining whether the at least one object image match the at least one checking image by comparing the at least one object image and the at least one checking image,
wherein the image sensor module captures the at least one object image toward the carrying surface along an axial direction, and the axial direction is perpendicular to the carrying surface,
wherein the step of obtaining the at least one checking image associated with the layer objects based on the three-dimensional model information and the at least one view angle comprises:

converting the three-dimensional model information to obtain a plurality of cross-sectional views of each of the layer objects projected on the carrying surface; and
stacking the cross-sectional views to obtain the at least one checking image corresponding to the at least one view angle.

20. A three-dimensional printing apparatus, comprising:
a movable platform, comprising a carrying surface;
a printing unit, disposed above the movable platform and forming at least one layer object on the carrying surface based on a three-dimensional model information;
an image sensor module, disposed above the movable platform to capture an object image of the at least one layer object in a capturing direction; and
a control unit, coupled with the printing unit and the image sensor module, wherein the control unit determines a checking image based on the three-dimensional model information and the capturing direction and compares the object image with the checking image,
wherein the image sensor module is disposed at one side of the movable platform, the three-dimensional printing apparatus further comprises a screen, the screen is disposed at the other side of the movable platform opposite to the image sensor module, the capturing direction of the image sensor module is toward the screen, and the capturing direction is parallel to the carrying surface.

21. A method for detecting a printing anomaly adapted for a three-dimensional printing apparatus comprising an image sensor module and a movable platform, wherein the three-dimensional printing apparatus forms a plurality of layer objects on a carrying surface of the movable platform based on three-dimensional model information to constitute a three-dimensional object comprising the layer objects, the method for detecting the printing anomaly comprising:
using the image sensor module to capture at least one object image of the three-dimensional object from at least one view angle;
obtaining at least one checking image associated with the layer objects based on the three-dimensional model information and the at least one view angle; and
determining whether the at least one object image match the at least one checking image by comparing the at least one object image and the at least one checking image,
wherein the image sensor module is disposed at one side of the movable platform, the three-dimensional printing apparatus further comprises a screen disposed at the other side of the movable platform opposite to the image sensor module, and the image sensor module captures the at least one object image toward the screen in a capturing direction, the capturing direction being parallel to the carrying surface.

* * * * *